US008360975B1

(12) United States Patent
Schwieterman et al.

(10) Patent No.: US 8,360,975 B1
(45) Date of Patent: Jan. 29, 2013

(54) NETWORKED INTERFACE APPLIANCE FOR IMPROVED MEDICAL DEVICE INTEGRATION AND PHYSICIAN WORKFLOW

(75) Inventors: Thomas D. Schwieterman, Coldwater, OH (US); Ruomei Zhang, Cerritos, CA (US); Philip Reichl, Simi Valley, CA (US)

(73) Assignee: Midmark Corporation, Versailles, OH (US)

( * ) Notice: Subject to any disclaimer, the term of this patent is extended or adjusted under 35 U.S.C. 154(b) by 874 days.

(21) Appl. No.: 12/036,950

(22) Filed: Feb. 25, 2008

(51) Int. Cl.
*A61B 5/00* (2006.01)
(52) U.S. Cl. .................... 600/300; 340/539.12; 709/255; 370/908; 370/913
(58) Field of Classification Search .......... 600/300–301; 705/2–9; 128/920–925, 903, 904
See application file for complete search history.

(56) References Cited

U.S. PATENT DOCUMENTS

| 6,551,243 | B2 * | 4/2003 | Bocionek et al. ............. 600/300 |
| 6,816,437 | B1 | 11/2004 | Teller et al. |
| 7,053,831 | B2 | 5/2006 | Dempsey et al. |
| 7,099,895 | B2 | 8/2006 | Dempsey |
| 7,571,308 | B1 * | 8/2009 | Bahl et al. ...................... 713/151 |
| 7,576,694 | B2 * | 8/2009 | Anjum et al. ................. 342/464 |
| 7,791,467 | B2 * | 9/2010 | Mazar et al. .................. 340/531 |
| 2005/0102167 | A1 * | 5/2005 | Kapoor ............................. 705/3 |
| 2006/0242293 | A1 * | 10/2006 | Russ ............................. 709/224 |
| 2007/0010721 | A1 * | 1/2007 | Chen et al. ..................... 600/300 |
| 2007/0135866 | A1 * | 6/2007 | Baker et al. ..................... 607/60 |
| 2008/0097912 | A1 * | 4/2008 | Dicks et al. ..................... 705/50 |
| 2008/0215120 | A1 * | 9/2008 | Dicks et al. ..................... 607/60 |

OTHER PUBLICATIONS

Lim, H. et al "Zero-Configuration, Robust Indoor Localization: Theory and Experimentation", Technical Report No. UIUCDCS-R-2005-2629 (Engr. No. UILU-ENG- 2005-1818), Aug. 2005.*
I. Burbey, "Systems for Sensing location Indoors", Burbey Qualifier, Feb. 2005, Bradley Department of Electrical and Computer Engineering, VA Tech.*
S. B. Gorthi, "Real -time data monitoring and manipulation for wireless sensor networks", Presented to the Faculty of the Graduate School of the University of Texas at Arlington in Partial Fulfillment of the Requirements for the Degree of Master of Science in Electrical Engineering, University of Texas at Arlington, May 2006.*
Kindberg, T. et al. "Validating and securing spontaneous associations between wireless devices", Mobile and Media Systems Laboratory HP Laboratories Palo Alto, HPL-2002-256, Sep. 12, 2002.*

(Continued)

*Primary Examiner* — Sam Yao
*Assistant Examiner* — Marie Archer
(74) *Attorney, Agent, or Firm* — Wood, Herron & Evans, LLP (57) ABSTRACT

A networked interface appliance for use in the medical arena that simplifies the connectivity of medical diagnostic devices to the portable computers in electronic medical record systems (EMR's). The appliance utilizes location support hardware and software to locate and map various tagged assets within the existing environment. The appliance automatically determines the proximity of nearby portable assets and computing devices, and creates network connection to each. Data obtained from a diagnostic device connected to the appliance is buffered and transmitted to portable computing devices connected to the appliance. Using specific IP addressing, support teams can connect to the appliance to diagnose and correct problems remotely using a local area network, wide area network or the Internet. A video port for remotely controlled video display and for local data acquisition is included. Location data from the appliance can be utilized in improving billing algorithms and workflow analysis. Asset management and location mapping of resources are also supported.

27 Claims, 3 Drawing Sheets

OTHER PUBLICATIONS

NPL_Midmark. pdf, p. 1-2.*
NPL_Memsic. pdf, p. 1-2.*

NPL_ARM920T.pdf, p. 1-12.*

* cited by examiner

NETWORKED INTERFACE APPLIANCE FOR IMPROVED MEDICAL DEVICE INTEGRATION AND PHYSICIAN WORKFLOW

TECHNICAL FIELD

This invention generally relates to improving medical workflow efficiency and asset management in medical service delivery.

BACKGROUND

The medical services industry has sought for several years to utilize technology to improve medical workflow efficiency. Specifically, physicians desire to transition from paper based records to electronic health record systems. At the same time, diagnostic devices are being enhanced to include digital technology and to provide digital communication interfaces for communication with external information systems.

Unfortunately, it has been difficult to achieve the ultimate goal of combining the existing devices and documentation systems into a single integrated system. This ultimate objective is frustrated by a number of factors. Firstly, PC's typically have a limited input/output capability, that is, a limited number of ports of various types required. Laptops and tablet or palmtop computers are often limited in their connections. Furthermore, PC's typically do not have the appropriate software (application software as well as operating system software and device drivers) needed to communicate with the wide variety of medical devices that are in common use. Furthermore, even if there was a PC configured to overcome these problems, the end user would be required to deal with a jumble of wires and interconnections to properly connect to the equipment relating to a particular patient. This is a particularly problematic issue if the PC is a mobile device, intended to travel with the medical professional, in which case the required connections and disconnections become a major inconvenience.

One approach to avoid the inconveniences just mentioned is to use networked communications. In the current state of the art, there are a wide variety of network adapters that can be used to connect multiple medical devices to a network so that data may be exchanged with electronic medical records systems. However, configuration of those network devices is complicated and requires significant technical support. The configurations are generally static in nature (for example, a specific serial port adapter is mapped to a static IP address, and then that static IP address is monitored by a PC to communicate with the device). When medical devices, computers and personnel move around in the healthcare organization, these static relationships need to be reconfigured, resulting in inconvenience to patients and healthcare providers.

Networking errors are common when using static IP addressing, and in a medical environment, those errors can be life threatening. Consider, for example, two ECG devices in different examination rooms, connected to a common network. A healthcare professional configuring a computer to monitor a patient (e.g., a mobile computer connected to the network via wireless network) will have no easy basis to determine which ECG is associated with a given IP address. Although the user could be presented with a list of ECG devices on the network, the time and energy spent in selecting the correct choice slows the workflow, and there is a risk that the wrong ECG device is selected, which can lead to a misdiagnosis and other threats to the patient. What is needed is a device that resolves these issues, provides interfaces to many types of medical devices and can automatically establish the correct network connections between those medical devices and the appropriate computers and applications in a dynamic, mobile environment.

In addition to the inefficiencies in device integration, there also exists a level of inefficiency in the medical arena with respect to asset management and workflow for medical and ancillary staff. Understanding the real time locations of physicians, nurses, staff, patients, devices, and other high value entities would provide tremendous immediate improvement in workflow. In addition to on-the-spot locating abilities, the ability to analyze patterns and problems using long term data for these mobile entities in the office could prove extremely valuable to making medical care more productive, efficient, reliable, safe, and profitable.

SUMMARY OF THE INVENTION

The networked interface appliance, and the system in which it is used, addresses the above needs.

In accordance with one aspect, the invention features an interface appliance which interconnects with a statically interfaced device and a dynamically interfaced devices within a specified area (such as an exam room). The statically interfaced device (such as medical diagnostic devices like electrocardiograms (ECG), spirometers, blood pressure meters, x-ray and video equipment) interfaces with the appliance using existing interface technologies such as Universal Serial Bus (USB) ports, serial ports, infrared, BLUETOOTH®, including IEEE 802.15, or other interface methodologies. The dynamically interfaced device (such as a portable computer being used by physicians to receive data from or control diagnostic equipment, or mobile diagnostic equipment) interfaces with the appliance using an internet protocol network. To establish this internet protocol network connection, a beacon signal is transmitted between the dynamically interfaced device and interface appliance, which includes an identifier unique to the transmitting device. A beacon listener receives the beacon signal, and when a beacon signal is detected, the identifier in the wireless beacon signal is used to establish communication between the interface appliance and the dynamically interfaced device over the internet protocol network, thereafter allowing the interface appliance to communicate with the dynamically interfaced device.

In specific embodiments, the beacon signal is transmitted by the interface appliance, and received by the dynamically interfaced device, and the dynamically interfaced device establishes communication with the interface appliance by transmitting a broadcast message over the internet protocol network, the message incorporating the identifier received from the wireless beacon signal and the internet protocol address of the dynamically interfaced device. The interface appliance receives this broadcast message, and upon identifying that its own identifier is included within the broadcast message, responds with a handshake message to the internet protocol address that originated the broadcast message, so that the interface appliance and the dynamically interfaced device thereafter possess each other's internet protocol addresses for future communication.

In an alternative embodiment, the beacon signal is transmitted by the dynamically interfaced device, and received by the interface appliance, the broadcast message is transmitted by the interface appliance, and the handshake message is transmitted by the dynamically interfaced device. In this embodiment, the handshake message may further identify the attributes of the dynamically interfaced device, enabling the interface appliance to identify possible future communications.

In one specific implementation, the dynamically interfaced device is a PC, mobile computer, palmtop, laptop, or other mobile computing device, utilizing medical diagnostic or record software, and the interface appliance includes interfaces to various medical diagnostic equipment, such that the medical diagnostic or record software may connect to and receive data from the diagnostic equipment as part of analyzing a patient's condition and/or developing a patient care record. Furthermore, the medical diagnostic or record software may control the diagnostic equipment via the interface appliance. In such applications, the interface appliance may also act as a data buffer, using memory within the interface appliance to buffer data received from the medical diagnostic equipment for transmission to the dynamically interfaced device over the internet protocol network, thus improving the reliability of the medical data.

In further implementations, the dynamically interfaced device may be a medical diagnostic device coupled to the Internet protocol network (such as a portable X-ray or portable ECG), and the interface appliance interfaces to the medical diagnostic device to facilitate communication between the medical diagnostic device and other dynamically interfaced devices which connect to the interface appliance in the manner described above. It is also possible that the dynamically interfaced devices interface with each other via the Internet protocol network.

The interface appliance may further include a storage interface for connection to removable storage devices such as secure digital cards (SD cards), flash memory cards, USB flash memory drives, and memory sticks. Data within the storage devices connected to the interface appliance may be made available to dynamically interfaced devices connected thereto. The interface appliance may further use such storage devices to store data received from dynamically and statically interfaced devices for later use.

In the detailed embodiment described below, the interface appliance utilizes an operating system permitting remote access to data from and control of dynamically and statically interfaced devices connected to the interface appliance. In addition, the interface appliance permits access to internal functions thereof via the internet protocol network, facilitating remote support and maintenance. In a related functionality, the interface appliance operating system may include a diagnostic routine for detecting malfunctions of the interface appliance or of devices interfaced thereto, and generating messages over the internet protocol network in the event of detection of such malfunctions.

In the specific embodiment described herein, the wireless beacon signal comprises a combined radio frequency and ultrasonic signal, such as the combined radio frequency and ultrasonic signaling used in the Cricket technology developed at the Massachusetts Institute of Technology. In this embodiment, the dynamically interfaced device and/or the interface appliance utilizes a Cricket listener for identifying nearby beacons and the proximity thereof to the listener. In the event the proximity between the beacon and listener is known, as can be achieved using the Cricket technology, the interface appliance may establish communication with dynamically interfaced devices which meet a certain proximity criterion, such those devices closer than a predetermined distance from the interface appliance.

In a further embodiment, managed assets (such as valuable portable devices, personnel such as medical staff and physicians, and customers or patients) are identified by the interface appliance or by a mobile computing device through the use of wireless beacon signals. For example, such assets may generate wireless beacon signals with unique identifiers, received by the interface appliance. The interface appliance may deliver the identifiers received from the additional managed assets to an asset tracking database. If the asset tracking database receives identifiers from plural interface appliances at plural locations, and each interface appliance is associated with its location, the asset tracking database can provide real time tracking of the managed assets. Furthermore, the asset tracking database may permit analysis of workflow, scheduling, equipment utilization, and intra-office communications, and be used for service billing and payroll time entry.

It will be appreciated that the interface appliance described above may improve existing electronic medical record systems, by permitting automatic proximity-based selection and control of medical diagnostic equipment. A physician or staff member carrying a portable computing device can be automatically connected to the medical data for a patient upon entering the patient's room or approaching the patient, thus improving efficiency.

Furthermore, the asset management and proximity detection functions described above may further simplify workflow and improve security; for example, a portable computing device connected with an interface appliance, can detect through the interface appliance whether a physician or staff member is in the vicinity of the portable computing device. If not, the portable computing device may prevent access until a physician or staff member returns. This can prevent the portable computing device from providing access to patient records to unauthorized persons. Furthermore, because the portable computing device may verify that the physician or staff member logged into the device is present in the same location as the portable computing device, the integrity of the medical records may be improved, by verifying that the person logged into the portable computing device is in its vicinity during activities conducted under that persons login identity.

In a further embodiment, the interface appliance may provide a video interface. The interface may be used to deliver video to the proximity of the appliance, such as television signals, educational video and organizational news reports. Further, the video interface may permit the receipt of video from the proximity of the appliance.

Various features discussed below in relation to one or more of the exemplary embodiments may be incorporated into any of the above-described aspects of the present invention alone or in any combination. Again, the brief summary presented above is intended only to familiarize the reader with certain aspects and contexts of the present invention without limitation to the claimed subject matter.

BRIEF DESCRIPTION OF THE FIGURES

Various features, aspects, and advantages of the present invention will become better understood when the following detailed description is read with reference to the accompanying figures in which.

DETAILED DESCRIPTION OF EXEMPLARY EMBODIMENTS

One or more specific embodiments of the present invention will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Figure 1:
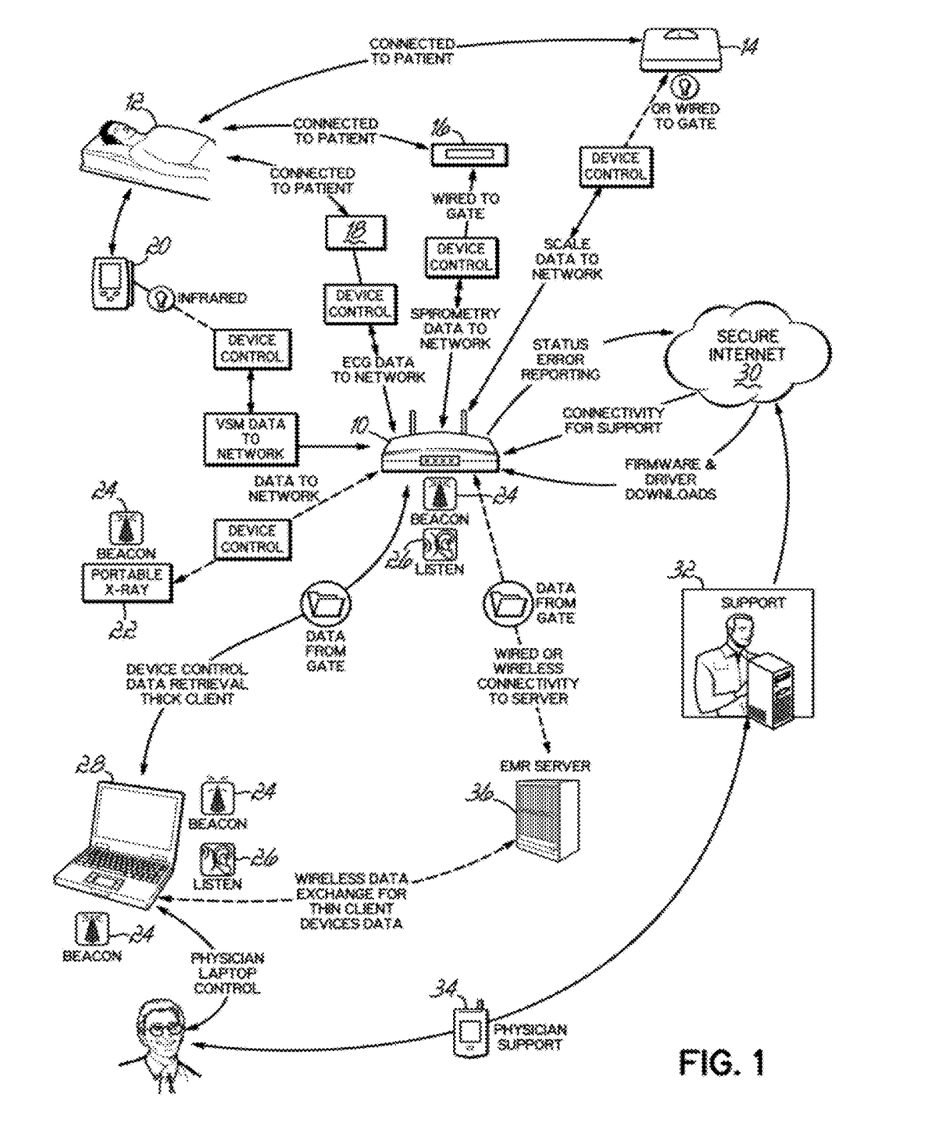
FIG. 1 is block diagram of a medical diagnostic environment utilizing an interface appliance in the form of a medical diagnostic gate.

Referring now to FIG. 1, the present invention will be described in connection with a medical diagnostic environment, in which the interface appliance forms a medical diagnostic gate 10 forming a communications hub for a plurality of medical diagnostic devices. Gate 10 is a network appliance built in a hard case enclosure designed to be located on a desktop, on a wall, within an exam table, or directly interfaced within a device (such as a vital sign monitor (VSM)). In one embodiment, this appliance has a Windows compliant processor board as its backbone, with necessary onboard hardware for 100 mbps Ethernet connectivity to an Internet protocol network and 802.11 (a, b, g and/or n) wireless networking, enabling connectivity to other network connected devices such as a physician PC or other mobile computing device 28, an electronic medical records (EMR) server 36, any network-enabled medical equipment such as an x-ray 22, and the public Internet 30.

Gate 10 includes 4 universal serial bus (USB) ports, US-232 serial port, Bluetooth® connectivity, and an infra-red emitter and reader, each to permit connectivity to medical diagnostic devices, including a scale 14 (e.g., a Seca Model 882, Tanita Model BF-350 or A&D Model UC-321 P connected via wired or wireless infrared communication), spirometry device 16 (connected via wired communication), ECG device 18 (connected via wired communication), vital signs monitor (VSM) 20 (delivering blood pressure, pulse and temperature signals via wired or wireless infrared communication), a USB camera, and other medical diagnostic or monitoring equipment connectable via USB, RS-232, Bluetooth or infrared. The technology for providing connectivity to a wide variety of devices in this manner is available in products sold by the assignee of the present application in its IQ-mark product line, such as:

IQvitals Mobile Cart
Midmark IQcart™
Midmark IQclassic™
Midmark IQecg™
Midmark IQflex™
Midmark IQholter™
Midmark IQmanager™
Midmark IQspiro™
Midmark IQstress™
Midmark IQvitals™
Midmark IQvitals™ PC.

Gate 10 further includes a VGA video port and S-video port, enabling the delivery of video signals to an in-room monitor (not shown). The outgoing video port on gate 10 allows for display of patient education videos, patient directed history functions, broadcast television, or office productions. EMR server may utilize central software to determine the most appropriate video imagery for a given patient situation. Such software will have the capacity to direct the programs to be displayed locally based on logic that is sensitive to patient age, diagnoses, problem lists, user input, physician directed video, and other considerations.

Gate 10 further includes a secure digital (SD Card) port, a flash media card port, and a memory stick port, providing for storage an retrieval of data, such as data collected from diagnostic monitoring devices.

The surface of the cased enclosure of gate 10 includes light emitting diode lights which display status information regarding the gate 10, including power status, 'device connected', 'input data stream active', 'network linked' (solid)/ 'network transmission active' (fast blink). The surface of the gate 10 enclosure may further include a display, such as a single line alphanumeric display LCD display of 16 characters or similar. The display may be used to display an identifier of gate 10 to distinguish it from other gates, or for other status information useful when connecting diagnostic devices to gate 10.

The internal software of gate 10 incorporates an operating system for managing the functionality of the gate 10. In one embodiment, this internal software includes an operating system (e.g., Windows XP, XP embedded, Vista or Windows CE) that controls device drivers, memory management, and network functions. When devices are attached to gate 10 via any one of the various ports (USB, Serial, BLUETOOTH®, including IEEE 802.15), gate 10 automatically powers up the device, initiates communications with the external hardware, and informs the network of the device's availability at the specific gate location.

Gate 10 is further equipped with the "Cricket Location Support System" developed at the Massachusetts Institute of Technology and documented in U.S. Pat. No. 6,816,437 to Teller et al. and assigned to the Massachusetts Institute of Technology, the entirety of which is incorporated herein by reference. Cricket technology is further described in the paper entitled "The Cricket Location-Support System" by Priyantha, Chakraborty and Balakrishnan, 6⇆ International Conference on Mobile Computing and Networking (ACM MOBICOM), Boston, Mass. August 2000 and incorporated herein in its entirety.

The Cricket technology utilizes a beacon signal comprising a simultaneous pulse of ultrasound and radiofrequency waves to determine the distance between beacons and listeners with respect to each other. Software, made available from the Massachusetts Institute of Technology as public domain, uses a logic algorithm to accurately determine locations of the beacons through mathematical analysis of the ultrasonic and radiofrequency signal timing.

The beacon component 24 included in gate 10 periodically generates a combined ultrasonic/radiofrequency signal to be utilized in proximity detection by wireless computing devices such as laptop computer 28, as discussed below with reference to FIGS. 2A to 2C. Each mobile computing device has a USB driven listening device 26 that provides capabilities that will used to detect beacon signals from nearby gate appliances and initiate the network conversation using either wireless or wired network protocols and embedded software as discussed in further detail below.

The Cricket listening component 26 included in gate 10 periodically detects other beacons 24 that are within the range of the listener 26. Beacons 24 are attached to assets within the medical facility such as a portable X-ray 24. Beacons 24 utilize small circuit boards that include controlled ultrasound and radiofrequency emitters. Cricket circuit boards are currently publicly available through Crossbow Technology, Inc., 4145 N. First Street, San Jose, Calif. 95134. This device may be condensed to smaller size so that it may be attached to, or carried by, objects or people.

As discussed below, listener component 26 of gate 10 monitor the local environment and relay each discovered object's identifier to the internet protocol network. Software within an asset tracking database server may then, based on a known location of the gate, plot the location of each object in a facility map, and store that data for future analysis. Analysis of each asset's location on a day to day basis may permit workflow improvement.

Gate 10 also connects to electronic medical record software in an EMR server 36. Specifically, gate 10 periodically generates internet protocol messages directed to EMR server 36 to notify server 36 that gate 10 is on-line and, optionally, to notify server 36 of the current capabilities of the diagnostic equipment connected to gate 10. In one embodiment, after establishing such communication, gate 10 continuously feeds data from the diagnostic equipment connected to gate 10, to EMR server 36 so that EMR server 36 may store this information and/or provide a feed of this information to other destinations such as a mobile computing device 28 being used by a physician or staff member visiting the patient or monitoring the patient from a remote location.

Gate 10 may also connect to EMR server 36 to provide real time tracking of assets identified as in the vicinity of gate 10. One asset that can be tracked is a physician or staff person, or the mobile computing device 28 being carried by a physician or staff person. In response to a physician, staff member or mobile computing device entering the vicinity of the gate 10, EMR server 36 may automatically load a patient's electronic record on the mobile computing device 28. Furthermore, EMR server 36 may evaluate whether a physician or staff person is in the same room as mobile device 28, to automate physician/staff log-in to the mobile device 28, or lockout the mobile device 28 in the event of the absence of authorized personnel in the vicinity of the wireless computing device. Furthermore, EMR server may log the time spent by a physician or staff with a patient for billing purposes, may log whether there is a 'witness present' during sensitive examinations requiring a second staff person present, and may accumulate various additional data to assist with EMR workflow analysis (such as patient waiting and scheduling time). These features may aid in improving physician workflow as well by providing instruction on current location of patients, next patient to be seen, etc.

Gate 10, when acquiring medical diagnostic data, serves as an electronic data buffer for the acquired data. Internal memory in gate 10 will save the data stream, allowing a controlled data transmission to a client (mobile computing device 28, EMR server 36), that is dynamic in response to the available network speed. Gate 10 can thus improve the data obtained by the EMR or mobile device 28 from the medical diagnostic device by improving accuracy and completeness. Failed data transfers will be stored locally within gate 10 until the communication problem is resolved. When communication is re-established, the gate will continue the transmission using stored data. Local ports on gate 10, such as the SD slot or memory stick slot, can be used to back up the data should the network fail consistently.

It will be appreciated that mobile computing device 28 may operate in a "thin client" mode in which data is delivered to EMR server, and displays generated at EMR server 36 summarizing that information are presented at mobile device 28, or mobile computing device 28 may operate in a "thick client" mode in which data is delivered from gate 10 directly to mobile computing device 28 for interpretation and storage within the portable device 28.

Gate 10 is connectable using secure internet protocol communication 30, to the intranet of the medical facility and/or (via a router or gateway) to the public Internet. Support staff 32 located within the medical facility's intranet, or at a remote location connected the public Internet, may use the gate 10's internal internet protocol (IP) address to connect to the operating system within gate 10, for example in response to a support telephone call placed by a physician over the physician's wireless telephone 34. The operating system of gate 10 supports log-in to the device for diagnosis of malfunctions and remote correction of internal errors. In addition, the support staff may also perform firmware and driver downloads to gate 10 from a remote location. In addition, the device may perform automatic diagnostics and deliver email or other Internet-compatible messages to support team members in the event of problems, potentially prior to awareness by the end user.

Figure 2A:
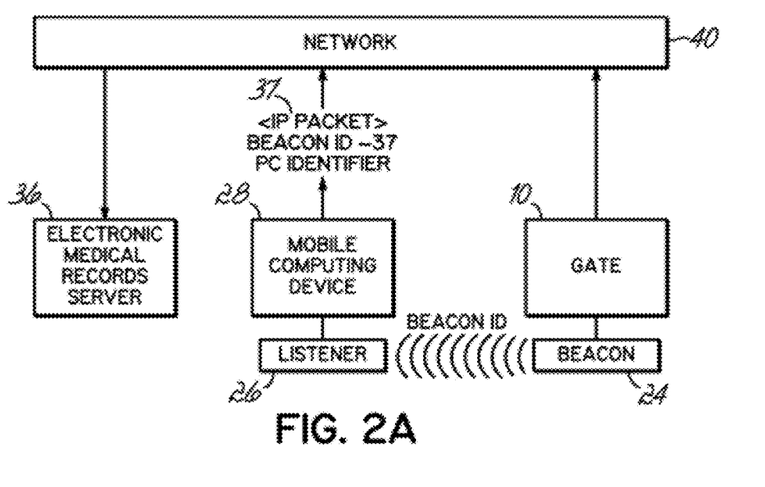
FIGS. 2A-2C are network diagrams illustrating the connectivity of a mobile computing device to a medical diagnostic gate via a network, and illustrating the delivery of a beacon signal from the gate to the device and responsive broadcast, handshake and service request packet exchanges.

Referring now to FIG. 2A, the interaction of a mobile computing device 28 and a gate 10 can be elaborated. Gate 10, computing device 28 and EMR server 36 are each connected to an internet protocol network backbone 40. The connection of gate 10 to network 40 may be wired or wireless, as noted above. Mobile computing device 28 typically is connected wirelessly to network 40 and EMR server 36 is typically connected via 100 Mbps Ethernet to backbone 40.

An interaction of a mobile computing device 28 and gate 10 is initiated by the delivery of a wireless beacon signal from beacon 24 associated with gate 10 to a listener 26 associated with mobile computing device 28. Device 28 captures the beacon identifier from the received beacon signal, and issues an internet protocol packet including the beacon identifier and its own identifier. In the event plural beacon signals are received, the identifier from the nearest beacon (as determined using the above-referenced Cricket logic) is used. In the event multiple beacons are seen but at least one beacon lacks location information, the ambiguity needs to be resolved. In one embodiment, the identifiers of each of the beacons (which may be intuitive text names) are presented to the user for the user to select the desired beacon.

In a thin client implementation of the invention, gate 10 initially delivers all medical diagnostic data to EMR server 36, and mobile computing device receives this data from EMR server 36 by delivering the internet protocol packet 37 to EMR server 36, so that EMR server 36 may identify mobile computing device 28 as within the vicinity of gate 10, and begin delivery of medical diagnostic information received from gate 10 to mobile computing device 28.

In a thick client implementation of the invention, a connection is established from gate 10 directly to mobile computing device 28. To accomplish this, mobile computing device 28 must learn the IP address of the gate 10 that issued the beacon signal. In this case, the internet protocol packet 37 issued by mobile computing device 28 in FIG. 2A is a broadcast packet, issued to all nodes on the local network, including gate 10.

Figure 2B:
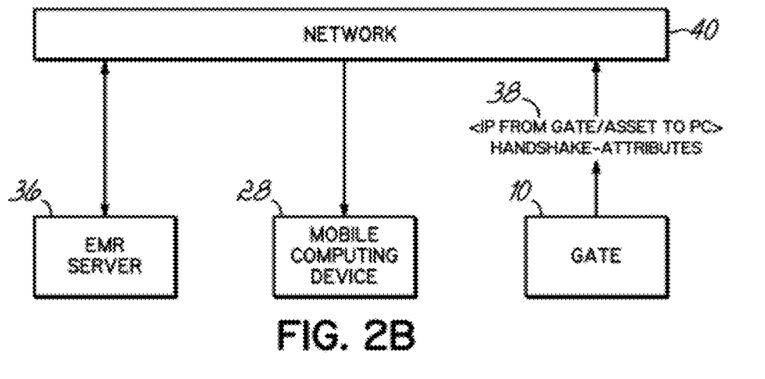
Figure 2C:
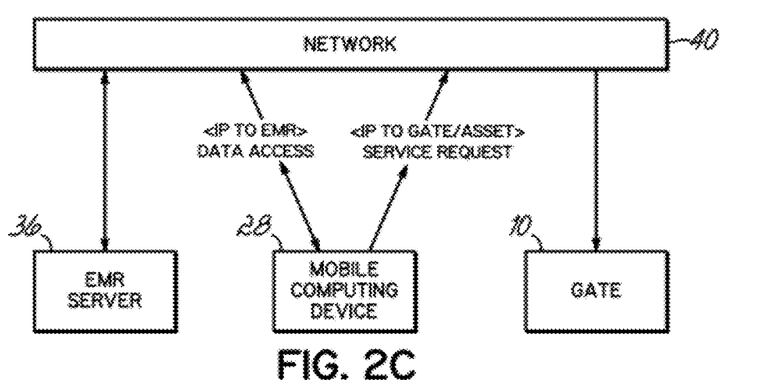

Gate 10, upon receipt of this broadcast packet, responds as shown in FIG. 2B by delivering a handshake IP packet 38 identifying the gate 10 and its device attributes (i.e., data streams provided, etc.) This packet is directed to the return address of the broadcast packet issued by mobile computing device 28, and as such is returned to mobile computing device 28. When this packet is successfully received in response to a broadcast message, mobile computing device 28 may respond by issuing a service request to gate 10 to begin streaming of medical diagnostic information from gate 10. Mobile computing device 28 may further issue data access requests to EMR server 36 to retrieve the medical record for the patient in the current proximity of gate 10 and to combine this information with incoming diagnostic data from gate 10 to present on the screen of the mobile computing device.

It will be noted that mobile computing device 28 should properly handle error conditions such as the receipt of multiple responses to a broadcast packet, and the receipt of such responses without the prior transmission of a broadcast packet. Both conditions indicate an address conflict or other malfunction which may be notified to the administrator or otherwise handled appropriately.

Figure 3A:
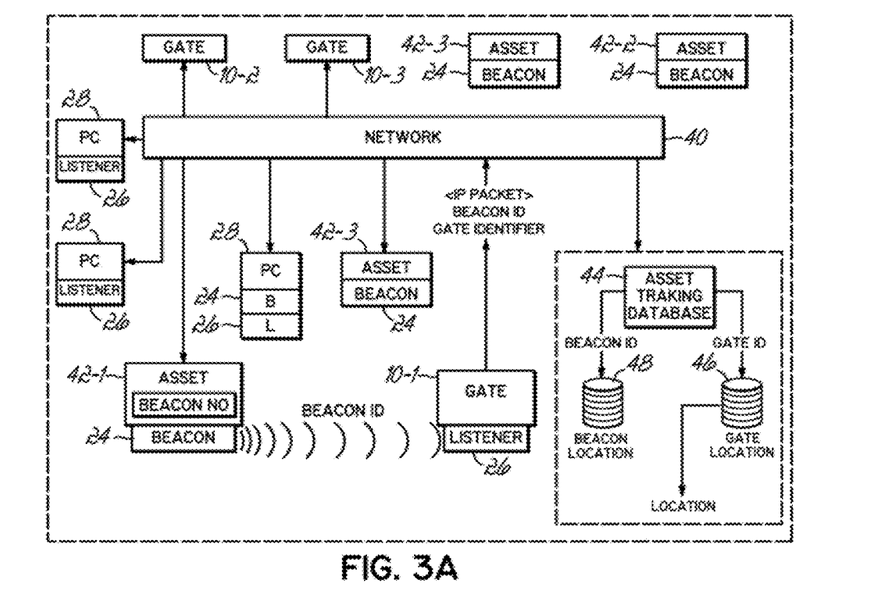
FIG. 3A is network diagram illustrating a more complete implementation of the invention in a medical diagnostic environment, including multiple gate devices for each of several local areas, multiple PC/mobile computing devices, and multiple assets (persons, objects), the locations of which are tracked, in which a mobile asset beacon signal is received by a listener at a gate.

Referring now to FIG. 3A, in a more complex implementation of the invention, the computing environment may include a plurality of gates 10, 10-1, 10-2, 10-3, each associated with its own location. Each gate, however, is assigned a unique identifier and a unique IP address (typically by a dynamic host configuration protocol (DHCP) server), as a consequence of which only one gate will respond to a broadcast message incorporating a beacon signal. Furthermore, plural mobile computing devices 28 move about the mobile computing environment and are dynamically connected with information regarding particular patients as they enter and leave the vicinity of those patients.

Additionally, in the embodiment of FIG. 3A, plural assets 42-1, 42-2 and 42-3 are associated with beacons 24, to allow tracking of the location of those assets. Specifically, the beacon 24 attached to an asset 42-1 issues a wireless beacon signal which, when in range, is received by the listener device on a gate 10-1. Gate 10-1 responds by originating an IP packet 43 incorporating the beacon identifier. This IP packet 43 is delivered to an asset tracking database 44 within EMR server 36. Within asset tracking database 44, the gate identifier is used as an index in a first table 46 associating each gate with its physical location, and then this physical location is stored along with the beacon ID for the asset in a second database 48, so that database 48 accumulates asset tracking data over time, for use in various ways as discussed above.

It will be noted that assets tracked in the manner described above, may include networked communications capabilities. For example, a portable x-ray device such as 22 shown in FIG. 1, may incorporate networked communication capability which may be accessed. In such a circumstance, the packet 43 issued in FIG. 3A may be a broadcast packet, receivable by the mobile asset 42. If mobile asset 42 includes a networked communications capability, asset 42 may respond to this broadcast message by delivering a responsive handshake message 45 identifying itself and/or its capabilities. Upon receipt of this responsive message, the gate 10 may then issue a service request 47 to the IP address of the asset 42-1 to begin use of its networked communications capability.

Figure 3B:
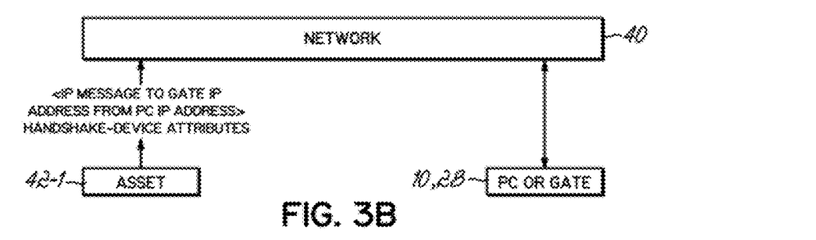
FIG. 3B illustrates an embodiment in which the mobile asset provides network-enabled functionality, and initiates a handshake response of to the broadcast signal issued thereto.
Figure 3C:
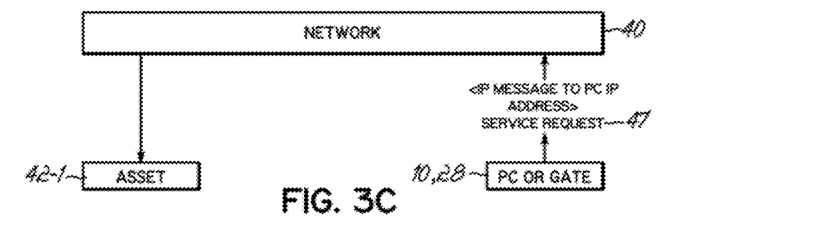
FIG. 3C illustrates a subsequent service request to the mobile asset.

It will be appreciated that the functionality described above for connecting to a mobile asset, may also be implemented in a mobile computing device. Specifically, a mobile computing device may listen for a beacon signal from an asset, deliver a responsive broadcast packet 43, receive a reply message 45, and issue a service request 47. In this manner networked communication with diagnostic devices may extend to devices that do not connect through gate 10 for network communication.

The invention has been described herein in substantial detail, however, it is not the Applicant's intention to be limited to such details which are presented for illustrative purposes. Specifically, when introducing elements of the present invention (E.G., the exemplary embodiments(s) thereof), the articles "a", "an", "the" and "said" are intended to mean that there are one or more of the elements. The terms "comprising", "including" and "having" are intended to be inclusive and mean that there may be additional elements other than the listed elements.

It will be noted that beacon technology other than Cricket may be used consistently with the present invention. Specifically, radiofrequency identification (RF-ID) technology may be used to generate and detect beacon signals. For example, RF-ID operating at 438 MHz at a power level less than 50 mW could be used without substantial interference in a medical environment, and would provide functionality for identifying proximity of mobile assets and mobile computing devices to gates 10 positioned about a medical facility, however, it is presently believed that Cricket offers advantages in its ability to measure proximity and in limiting connectivity to line-of-sight circumstances which may reduce the potential for making incorrect connections.

As various changes could be made in the above-described aspects and exemplary embodiments without departing from the scope of the invention, it is intended that all matter contained in the above description shall be interpreted as illustrative and not in a limiting sense.

What is claimed is:

1. An interface appliance for interconnecting with statically and
    dynamically interfaced devices within a specified area by the use of a remote beacon listener, the interface appliance comprising:
    an interface connector of the type used on personal computers for connection to a statically interfaced device,
    an internet protocol network interface,
    a wireless beacon signal device separate from said internet protocol network interface, and
    a controller,
    the wireless beacon signal device configured for transmitting a beacon signal to said remote beacon listener, the beacon signal including an identifier unique to the wireless beacon signal device,
    the controller configured for establishing an internet protocol connection with a dynamically interfaced device via the internet protocol network interface using the identifier incorporated into the wireless beacon signal, and thereafter communicating with the dynamically interfaced device.

2. The interface appliance of claim 1 wherein said internet protocol network interface comprises one or more of an Ethernet interface and an 802.11 wireless interface.

3. The interface appliance of claim 1, wherein said statically interfaced device comprises one or more of:
    an electrocardiogram (ECG) device,
    a spirometer device,
    a blood pressure meter,
    a pulse meter,
    a temperature meter,
    an x-ray device, and video equipment.

4. The interface appliance of claim 1 wherein said interface connector of the type used on personal computers comprises one or more of:

a Universal Serial Bus (USB) port,
an RS-232 serial port,
an infrared port, and
an IEEE 802.1x interface.

5. The interface appliance of claim 1, wherein said wireless beacon signal device is configured for transmitting said beacon signal incorporating an identifier unique to said interface appliance and receiving broadcast messages from a dynamically interfaced device.

6. The interface appliance of claim 5 wherein said internet protocol network interface is configured for receiving from said remote beacon listener device a broadcast message over the internet protocol network, the message incorporating the identifier included in the wireless beacon signal.

7. The interface appliance of claim 6 wherein said controller is configured for receiving said broadcast message and, upon recognition of said identifier in said broadcast message, responding with a handshake message to the internet protocol address originating said broadcast message, whereby said dynamically interfaced device and said interface appliance establish their respective internet protocol addresses for future communication.

8. The interface appliance of claim 1 wherein said dynamically interfaced device is a PC, mobile computer, palmtop, laptop, or other mobile computing device configured for executing medical diagnostic software, said interface appliance configured for supplying information received from said statically interfaced device to medical diagnostic software.

9. The interface appliance of claim 1 further comprising memory, wherein the interface appliance is configured for buffering data received from said statically interfaced device into said memory for subsequent transmission to said dynamically interfaced device over the internet protocol network.

10. The interface of claim 1 wherein said dynamically interfaced device is a PC, mobile computer, palmtop, laptop or other mobile computing device configured for executing medical diagnostic software, said interface appliance forwarding commands received from said medical diagnostic software to said statically interfaced device.

11. The interface of claim 1 wherein said dynamically interfaced device is a medical diagnostic device coupled to said internet protocol network, said interface appliance configured for interfacing to said medical diagnostic device via said internet protocol network to facilitate communication between the medical diagnostic device and other dynamically interfaced devices.

12. The interface appliance of claim 1 further comprising a storage interface configured for connection to a removable storage device.

13. The interface appliance of claim 12 wherein said removable storage device comprises one or more of a secure digital card (SD card), flash memory card, USB flash memory drive, and memory stick media.

14. The interface appliance of claim 12 wherein said controller is configured for storing data from the removable storage device to said dynamically interfaced device.

15. The interface appliance of claim 14 wherein said controller is configured for storing data received from said dynamically or statically interfaced devices in said removable storage device.

16. The interface appliance of claim 1, wherein said controller is configured for implementing an operating system permitting remote access thereto via said internet protocol network.

17. The interface appliance of claim 16 wherein said operating system comprises instructions to permit remote support and maintenance of said interface appliance via said internet protocol network.

18. The interface appliance of claim 1 wherein said controller performs is configured for performing a diagnostic routine for detecting malfunction of the interface appliance or of devices interfaced thereto, said diagnostic routine generating messages over the internet protocol network in the event of detection of a malfunction.

19. The interface appliance of claim 1 wherein said wireless beacon signal device is configured for transmitting a beacon signal which comprises a radio frequency and an ultrasonic signal.

20. The interface appliance of claim 19 wherein said wireless beacon signal device is configured for utilizing Cricket signaling.

21. The interface appliance of claim 1 wherein said controller is configured for establishing communication with a dynamically interfaced device which meets a certain proximity criterion.

22. An interface appliance for interconnecting with statically and dynamically interfaced devices within a specified area by the use of a beacon signal, the interface appliance comprising:
   an internet protocol network interface,
   a wireless beacon listener device separate from said internet protocol network interface, and
   a controller,
   the wireless beacon listener device configured for receiving a beacon signal from a remote beacon signal device, the beacon signal incorporating an identifier unique to a dynamically interfaced device,
   the controller configured for generating an internet protocol message via the internet protocol network interface using the identifier incorporated into the wireless beacon signal.

23. The interface appliance of claim 22 wherein said controller is configured for transmitting a message over said internet protocol network including said identifier, the message indicating the dynamically interfaced device is located in the vicinity of the interface appliance.

24. The interface appliance of claim 22 wherein said wireless beacon signal device is configured for transmitting beacon signals having unique identifiers, the interface appliance configured for storing identifiers received from the additional managed assets in an asset tracking database.

25. The interface appliance of claim 24 wherein said interface appliance is configured for storing identifiers from one or more of: valuable portable devices, personnel such as medical staff and physicians, customers or patients.

26. The interface appliance of claim 23 wherein said wireless beacon signal device is configured for transmitting a beacon signal which comprises a radio frequency and an ultrasonic signal.

27. The interface appliance of claim 26 wherein said wireless beacon listener device is configured for utilizing Cricket signaling.

* * * * *

UNITED STATES PATENT AND TRADEMARK OFFICE
CERTIFICATE OF CORRECTION

PATENT NO. : 8,360,975 B1  
APPLICATION NO. : 12/036950  
DATED : January 29, 2013  
INVENTOR(S) : Thomas D. Schwieterman et al.

It is certified that error appears in the above-identified patent and that said Letters Patent is hereby corrected as shown below:

FIG. 3A, #44 reads "Traking" and should read -- Tracking --

Column 2  
Line 24 reads "and a dynamically interfaced devices" and should read -- and a dynamically interfaced device --

Column 3  
Line 63 reads "such those devies closer" and should read -- such as those devices closer --

Column 4  
Line 58 reads "FIG. 1 is block disgram of a" and should read -- FIG. 1 is a block diagram of a --  
Line 66 reads "FIG. 3A is network disgram" and should read -- FIG. 3A is a network diagram --

Column 5  
Line 8 reads "response of to the broadcast signal" and should read -- response to the broadcast signal --

Column 6  
Line 20 reads "storage an retrieval of data" and should read -- storage and retrieval of data --  
Line 22 reads "The surface of the cased enclosure of gate 10" and should read -- The surface of the case enclosure of gate 10 --  
Line 28 reads "alphanumeric display LCD display of" and should read -- alphanumeric LCD display of --

Column 7  
Line 2 reads "will used to detect" and should read -- will be used to detect --  
Lines 16-17 read "component 26 of gate 10 monitor the . . . and relay each" and should read -- component 26 of gate 10 monitors the . . . and relays each --

Signed and Sealed this  
Ninth Day of April, 2013

Teresa Stanek Rea  
*Acting Director of the United States Patent and Trademark Office*

Column 8
Line 18 reads "location connected the" and should read -- location connected to the --

Column 10
Line 5 reads "it is not the Applicant's intention to" and should read -- it is not the Applicants' intention to --
Lines 7-8 read "elements of the present invention (E.G., the exemplary embodiments(s) thereof), the" and should read -- elements of the present invention (e.g., the exemplary embodiment(s) thereof, the --

Column 11
Line 35, Claim 10, reads "The interface of claim 1 wherein" and should read -- The interface appliance of claim 1 wherein --
Line 41, Claim 11, reads "The interface of claim 1 wherein" and should read -- The interface appliance of claim 1 wherein --

Column 12
Line 10, Claim 18, reads "performs is configured for" and should read -- is configured for --
Line 56, Claim 26, reads "The interface appliance of claim 23 wherein" and should read -- The interface appliance of claim 22 wherein --

UNITED STATES PATENT AND TRADEMARK OFFICE
CERTIFICATE OF CORRECTION

| | | |
|---|---|---|
| PATENT NO. | : 8,360,975 B1 | |
| APPLICATION NO. | : 12/036950 | |
| DATED | : January 29, 2013 | |
| INVENTOR(S) | : Thomas D. Schwieterman et al. | |

It is certified that error appears in the above-identified patent and that said Letters Patent is hereby corrected as shown below:

In the Drawings:

FIG. 3A, #44 reads "Traking" and should read -- Tracking --

In the Specifications:

Column 2
Line 24 reads "and a dynamically interfaced devices" and should read -- and a dynamically interfaced device --

Column 3
Line 63 reads "such those devies closer" and should read -- such as those devices closer --

Column 4
Line 58 reads "FIG. 1 is block diagram of a" and should read -- FIG. 1 is a block diagram of a --
Line 66 reads "FIG. 3A is network diagram" and should read -- FIG. 3A is a network diagram --

Column 5
Line 8 reads "response of to the broadcast signal" and should read -- response to the broadcast signal --

Column 6
Line 20 reads "storage an retrieval of data" and should read -- storage and retrieval of data --
Line 22 reads "The surface of the cased enclosure of gate 10" and should read -- The surface of the case enclosure of gate 10 --
Line 28 reads "alphanumeric display LCD display of" and should read -- alphanumeric LCD display of --

This certificate supersedes the Certificate of Correction issued April 9, 2013.

Signed and Sealed this
Twenty-eighth Day of May, 2013

Teresa Stanek Rea
*Acting Director of the United States Patent and Trademark Office*

CERTIFICATE OF CORRECTION (continued)
U.S. Pat. No. 8,360,975 B1

Column 7
Line 2 reads "will used to detect" and should read -- will be used to detect --
Lines 16-17 read "component 26 of gate 10 monitor the . . . and relay each" and should read
-- component 26 of gate 10 monitors the . . . and relays each --

Column 8
Line 18 reads "location connected the" and should read -- location connected to the --

Column 10
Line 5 reads "it is not the Applicant's intention to" and should read -- it is not the Applicants' intention to --
Lines 7-8 read "elements of the present invention (E.G., the exemplary embodiments(s) thereof), the" and should read -- elements of the present invention (e.g., the exemplary embodiment(s) thereof, the --

In the Claims:

Column 11
Line 35, Claim 10, reads "The interface of claim 1 wherein" and should read -- The interface appliance of claim 1 wherein --
Line 41, Claim 11, reads "The interface of claim 1 wherein" and should read -- The interface appliance of claim 1 wherein --

Column 12
Line 10, Claim 18, reads "performs is configured for" and should read -- is configured for --
Line 56, Claim 26, reads "The interface appliance of claim 23 wherein" and should read -- The interface appliance of claim 22 wherein --